United States Patent [19]

Röhricht et al.

[11] 4,045,433

[45] Aug. 30, 1977

[54] 1,3,4,5-TETRAHYDRO-2H-1,4-BENZODIAZEPIN-2-ONES

[75] Inventors: Julia Röhricht; Lajos Kisfaludy; Laszlo Urogdi; Eva Palosi; Szabolcs Szeberenyi; Laszlo Szporny, all of Budapest, Hungary

[73] Assignee: Richter Gedeon Vegyeszeti Gyar Rt., Budapest, Hungary

[21] Appl. No.: 580,307

[22] Filed: May 23, 1975

[30] Foreign Application Priority Data

May 29, 1974 Hungary .............................. RI 538

[51] Int. Cl.$^2$ ........................................... C07D 243/24
[52] U.S. Cl. .............................. 260/239.3 D; 424/244
[58] Field of Search ................................. 260/239.3 D

[56] References Cited

U.S. PATENT DOCUMENTS

| 3,236,838 | 2/1966 | Archer et al. ............... 260/239.3 D |
| 3,551,415 | 12/1970 | Earley et al. ............... 260/239.3 D |

FOREIGN PATENT DOCUMENTS

| 2,150,075 | 4/1972 | Germany .................... 260/239.3 D |
| 25,199 | 7/1973 | Japan ........................ 260/239.3 D |

*Primary Examiner*—Henry R. Jiles
*Assistant Examiner*—Robert T. Bond
*Attorney, Agent, or Firm*—Karl F. Ross; Herbert Dubno

[57] ABSTRACT

An N-substituted carbonyl tetrahydrobenzodiazepines having ethoxycarbonyl, formyl, carbamoyl or methyl carbamoyl as the $N^4$ substituent.

2 Claims, No Drawings

1,3,4,5-TETRAHYDRO-2H-1,4-BENZODIAZEPIN-2-ONES

This invention relates to new benzodiazepine derivatives and pharmaceutical compositions containing the same, as well as to a process for the preparation thereof.

More particularly, the invention relates to the racemic $N^4$-acyl-1,3,4,5-tetrahydro-2H-1,4-benzodiazepine-2-one derivatives of the formula (I),

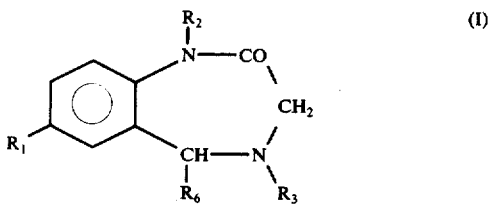

wherein $R_1$ hydrogen, halogen, trifluoromethyl, amino or nitro, $R_2$ is hydrogen or alkyl, $R_3$ is an acyl group derived from a carbonic acid derivative or from an substituted or unsubstituted aliphatic, cycloaliphatic or aromatic carboxylic acid, and $R_6$ is phenyl or halophenyl, with the proviso that i. if $R_2$ is lower alkyl and $R_1$ is hydrogen or halogen, $R_3$ may not be a carbamoyl group having a lower alkyl, lower alkenyl, cyclohexyl, phenyl or benzyl substituent, or ii. if $R_2$ is lower alkyl and $R_1$ is halogen or trifluoromethyl, $R_3$ may not be lower alkanoyl.

Furthermore, the invention relates to the optically active $N^4$-acyl-1,3,4,5-tetrahydro-2H-1,4-benzodiazepine-2-one derivatives of the formula (I), wherein $R_1$ is hydrogen, halogen, trifluoromethyl, amino or nitro, $R_2$ is hydrogen or alkyl, $R_3$ is an acyl group derived from a carbonic acid derivative or from an substituted or unsubstituted aliphatic, cycloaliphatic or aromatic carboxylic acid, and $R_6$ is phenyl or halophenyl.

All the above compounds are novel.

The compounds according to the invention possess primarily tranquillo-sedative activities.

Owing to their excellent tranquillo-sedative effects, some of the hitherto known 1,4-benzodiazepine derivatives have attained great practical use.

Based on the examination of the known compounds some conclusions can be drawn with respect to the relationship of the chemical structures and pharmaceutical effects. It was stated, inter alia, that the presence of a double bond between positions 4 and 5 absolutely necessary to obtain a compound with high activity, since the tetrahydro derivatives obtained by saturating this double bond showed far lower activities in every pharmacological tests than the respective unsaturated compounds. This low activity decreases further when a substituent is attached to position $N^4$(L. H. Sternbach et al.: Drugs Affecting the Central Nervous System (A. Burger ed.), 1968, vol. 2, page 237). These facts explain why the number of tetrahydro-benzodiazepine derivatives prepared heretofore is far lower than that of the dihydro compounds.

Up to now the following methods were utilized for the preparation of 4-substituted-tetrahydro-1,4-benzodiazepine derivatives:

1-Monosubstituted and 1,4-disubstituted tetrahydro-benzodiazepine derivatives were prepared by the direct alkylation of 1,4-tetrahydro-benzodiazepine (J. Med. Chem. 7, 386 (1964), French Pat. No. 1,339,762).

According to the U.S. Patent No. 3,501,474 and the Dutch Patent Application No. 69 17,320 the $N^4$-substituted tetrahydro-1,4-benzodiazepine-2-one derivatives were prepared from the appropriate isoquinoline compounds by ring expansion.

The Japanese Patent No. 48-25,199 describes the preparation of tetrahydro-1,4-benzodiazepine-2-one derivatives having a substituted carbamoyl group in position 4.

Contrary to the previous experiences we have found that the 4-substituted-tetrahydro-1,4-benzodiazepine derivatives of the formula (I) possess strong harmaceutical effects.

In these compounds $R_1$ is fluorine, chlorine, bromine or iodine, preferably chlorine, as the halogen atom.

As an alkyl group, $R_2$ is a straightchained or branched alkyl group, preferably a lower alkyl group with 1 to 6 carbon atoms. Such groups can be methyl, ethyl, n-propyl, isopropyl, n-butyl, isobutyl, t-butyl, amyl, isoamyl, and hexyl. A preferred alkyl group is methyl.

$R_3$ is an acyl group derived from various carbonic acid derivatives, such as carbonic acid, phosgene, haloformic acid esters, urethanes, ureides, and semicarbazides. These acyl groups can be halocarbonyl groups (preferably chlorocarbonyl group), oxycarbonyl derivatives of optionally substituted aliphatic, cycloaliphatic or aromatic hydrocarbons, aminocarbonyl aminocarbonyl having a hydrocarbyl substituent as defined above, acylaminocarbonyl to/groups, hydrazinocarbonyl group, and hydrazinocarbonyl groups having a hydrocarbyl or acyl substituent as listed above. In the hydrocarbyl-substituted aminocarbonyl groups the hydrocarbyl substituents may also form a ring together with the adjacent nitrogen atom, said ring may optionally contain one or more further hetero atoms, may have one or more substituents or may be condensed with another ring. The rings formed by the hydrocarbyl groups are preferably 5 to 7 membered saturated monocycles containing optionally one or more nitrogen, oxygen and/or sulfur atoms as further hetero atoms. Of the substituents attached optionally to the ring e.g. aliphatic or aromatic hydrocarbyl groups and the oxo group are mentioned. Particularly preferably substituents are the phenyl, alkyl and oxo groups. The number of substituents attached to the ring may range from 0 to 3. As mentioned above, the rings formed by the hydrocarbyl substituents may also be condensed with a further ring, preferably with a benzene ring. Of the preferred cyclic groups attached to the carbonyl group is position 4 of the benzodiazepine derivatives the pyrrolidino, piperidino, piperazino, 4-methylpiperazino, morpholino, and 1-methyl-2-oxo-5-phenyl-tetrahydro-1,4-benzodiazepine-4-yl are mentioned.

$R_3$ may stand further for an acyl group derived from an aliphatic, cycloaliphatic or aromatic carboxylic acid.

The acyl groups derived from aliphatic carboxylic acids can be acyl groups of saturated monocarboxylic acids (such as formic acid, acetic acid, propionic acid, isomeric valeric acids, etc.). The acyl groups can be those of unsaturated monocarboxylic acids (such as acrylic acid, crotonic acid, and vinylacetic acid, methacrylic acid. The hydrocarbyl chain of these acyl groups contain preferably 1 to 6 carbon atoms, and one or more substituents may be attached to said hydrocarbyl chain. Of these substituents the halogens (such fluorine, chlorine, bromine or iodine) attached to the same or different carbon atoms (e.g. monochloroacetyl, α,β-dibromopropionyl, trifluoroacetyl, and γ-chlorobutyryl), the oxo, amino, and aryl (such as phenyl, diphenyl, naphthyl, etc.) groups are mentioned.

The acyl groups derived from cycloaliphatic carboxylic acids may contain preferably a saturated or unsaturated mono- or polycyclic hydrocarbyl group with 5 to 20 carbon atoms, and may have optionally one or more alkyl, hydroxy, oxo, halogen, etc. substituents. Of these hydrocarbyl groups, those derived from cyclopentane, cyclohexane, tetrahydronaphthalene, menthane, methene, or bicyclic terpenes (such as cemphane, pinane, pinene, etc.) are to be mentioned.

The aromatic acyl groups may be derived from benzoic acid, diphenylcarboxylic acids or naphthoic acids. Optionally one or more substituent(s), such as a halogen atom or an alkyl, alkenyl, alkoxy, nitro, amino, hydroxy, trifluoromethyl, cyano, sulfo, thio or oxo group may be attached to the aromatic rings of said acyl groups.

The aliphatic hydrocarbon moieties of the acyl groups mentioned in connection with $R_3$ may be saturated or unsaturated hydrocarbyl groups. Of these groups the straight-chained or branched $C_{1-6}$ lower alkyl, alkenyl and alkynyl groups, furthermore the cycloaliphatic hydrocarbyl groups (especially the groups listed in the definition of the cycloaliphatic acyl groups) are preferred. The aromatic hydrocarbon groups are preferably mono- or polycyclic groups with 6 to 14 carbon atoms, such as phenyl, diphenyl or naphthyl, and may have one or more identical or different substituents, such as halogen, alkyl, alkenyl, alkoxy, nitro, amino, hydroxy, trifluoromethyl, cyano, sulfo, thio, oxo, etc.

As mentioned above, a halogen atom is optionally attached to the $R_6$ phenyl group. This halogen substituent can be fluorine, chlorine, bromine or iodine, and may attach preferably to the ortho position of the phenyl group.

The alkyl groups mentioned in the specification may be methyl, ethyl, n-propyl isopropyl, n-butyl, isobutyl, recrystallization isoamyl or isomeric hexyl groups. Of the alkoxy groups the straight-chained or branched $C_{1-6}$ lower alkoxy groups, such as methoxy, ethoxy, n-propoxy, isopropoxy, n-butoxy, isobutoxy, t-butoxy, amyloxy, isoamyloxy or isomeric hexyloxy groups are the most preferred. Of the alkenyl groups e.g. the allyl group; of the aryloxy groups e.g. the phenoxy, diphenyloxy or naphthoxy group; whereas of the aralkoxy groups e.g. the benzyloxy, phenethoxy, phenylpropoxy, phenylbutoxy, napthylmethoxy, napthylethoxy, naphthylpropoxy or naphthylbutoxy group is to be mentioned. These groups may have optionally one or more substitutents, e.g. halogen, alkyl, alkoxy, trifluoromethyl, hydroxy, nitro, etc.

The preferred representatives of the compounds having the formula (I) are those wherein
$R_1$ is halogen or nitro,
$R_2$ is hydrogen or alkyl, and
$R_3$ is a $C_{1-6}$ alkoxycarbonyl group (such as ethoxycarbonyl or butoxycarbonyl); an aralkoxycarbonyl group having optionally one or more substituent(s) (preferably a halo-substituted phenyl-$C_{1-6}$-alkoxycarbonyl group, such as p-chlorobenzyloxycarbonyl); an oxycarbonyl derivative of a $C_{5-10}$ unsaturated cycloaliphatic hydrocarbon (preferably an oxycarbonyl derivative of a monocyclic terpene, such as menthyloxycarbonyl); a carbamoyl group having optionally a $C_{1-6}$ alkyl, aryl, aralkyl or ($C_{1-6}$ alkyl-substituted)-aralkyl substituent (such as methylcarbamoyl, ethylcarbamoyl, butylcarbamoyl, phenylcarbamoyl, or a ($C_{1-6}$ alkyl-phenyl)-$C_{1-6}$-alkylcarbamoyl (e.g. methyl-benzylcarbamoyl) group); a $C_{1-6}$ alkylcarbonyl group having optionally e.g. a halogen, amino, protected amino (such as aralkoxycarbonylamido) or aryl substituent (such as glycyl, chloroacetyl, acetyl or phenylacetyl); an optionally substituted arylcarbonyl group (preferably a halo-substituted benzoyl group, such as o-chlorobenzoyl or p-chlorobenzoyl; or formyl.

Particularly effective are those compounds of the formula (I), wherein
$R_1$ is halogen or nitro,
$R_2$ is hydrogen or alkyl, and
$R_3$ is a $C_{1-6}$ alkoxycarbonyl group; a carbamoyl group having optionally a $C_{1-6}$ alkyl or methylphenyl-($C_{1-6}$ alkyl) substituent; a $C_{1-6}$ alkylcarbonyl group; a halo-substituted benzoyl group; or formyl group.

Even more preferred are those compounds of the formula (I), wherein $R_1$ is halogen or nitro, $R_2$ is hydrogen or lower alkyl, and $R_3$ is an optionally substituted carbamoyl group.

The most preferred representatives of the above compounds are those wherein $R_1$ is chlorine or nitro, $R_2$ is hydrogen or methyl, and $R_3$ is unsubstituted carbamoyl.

Of the compounds of the formula (I) 1-methyl-4-carbamoyl-5-phenyl-7-chloro-1,3,4,5-tetrahydro-2H-1,4-benzodiazepine-2-one has proved to be the most effective.

The compounds of the formula (I) can be prepared according to the invention as follows:

a) a 1,3,4,5-tetrahydro-2H-1,4-benzodiazepine-2-one derivative of the formula (II),

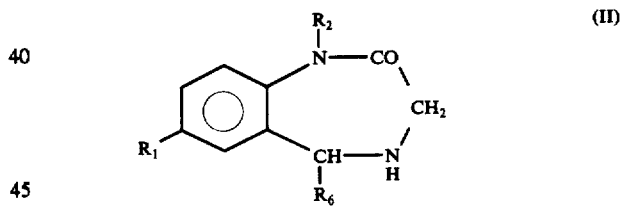

wherein $R_1$, $R_2$ and $R_6$ each have the same meanings as defined above, is reacted, optionally in the presence of an acid binding agent, with an acid derivative of the formula (III), R<sub>4</sub> - CO - X       (III)

prepared optionally directly in the reaction mixture from the apropriate carboxylic acid, wherein X is halogen or alkoxy, and $R_4$ is hydrogen halogen; an optionally substituted aliphatic, cycloaliphatic or aromatic hydrocarbyl group or an oxy derivative thereof; amino group; or an amino group having an optionally substituted amino, a hydrocarbyl (as defined above) or an acyl substituent, and, if desired, a thus-obtained compound of the formula (I), wherein $R_3$ is halocarbonyl, is reacted with ammonia or with an amine; or b) a 1,3,4,5-tetrahydro-2H-1,4-benzodiazepine-2-one derivative of the formula (II) or a salt thereof is reacted with a compound of the formula (IV), R<sub>5</sub> - Y       (IV)

wherein $R_5$ is hydrogen, alkali metal, or an aliphatic, cycloaliphatic or aromatic hydrocarbyl group and Y is a group of the formula NCO- or OCN-, and, if desired, any compound of the formula (I) wherein $R_2$ is hydrogen, is alkylated.

All the compounds prepared by the above process are novel.

The starting substances of the formula (II) can be prepared as described in Hungarian Pat. No. 155,251.

In the compounds of the formula (III) $R_4$ may represent fluorine, chlorine, bromine or iodine as halogen; a saturated or unsaturated, straight-chained or branched alkyl, alkenyl or alkynyl group with preferably 1 to 6 carbon atoms as aliphatic hydrocarbyl; a saturated or unsaturated mono- or polycyclic hydrocarbyl group with preferably 5 to 20 carbon atoms as cycloaliphatic hydrocarbyl; and a mono- or polycyclic hydrocarbyl group with preferably 6 to 14 carbon atoms as aromatic hydrocarbyl. These groups may have optionally one or more substituents.

The hydrocarbyl groups and the substituents, as well as the preferred representatives of the acyl groups are the same as listed in connection with the definition of $R_3$.

X may represent fluorine, chlorine, bromine or iodine as halogen, and a straight-chained or branched alkoxy group with preferably 1 to 6 carbon atoms (such as methoxy, ethoxy, n-propoxy, isopropoxy, n-butoxy, isobutoxy, t-butoxy, amyloxy, isoamyloxy or hexyloxy) as the alkoxy group.

In the starting substances of the formula (IV) $R_5$ is any alkali metal atom, but is preferably a potassium atom. When $R_5$ is an aliphatic, cycloaliphatic or aromatic hydrocarbyl group, it may represent those groups listed in connection with the definition of $R_4$.

When a compound of the formula (III), wherein X is halogen and $R_4$ has the same meanings as defined above, is used as starting substance in process variant a), the reaction is performed preferably in the presence of an acid binding agent in order to ensure a quick and complete reaction. As acid binding agent e.g. an inorganic base, such as a metal oxide, preferably an alkaline earth metal oxide (e.g. magnesium oxide), an alkali metal hydrocarbonate, such as sodium hydrocarbonate, an alkali metal carbonate, such as potassium carbonate, or a tertiary organic base, such as pyridine or a tertiary amine (e.g. triethylamine), etc. can be used. The amount of the acid binding agent may vary within wide limits, but the acid binding agent is used preferably at least in an amount necessary to bind all of the acid formed in the reaction. The reaction is carried out in an organic liquid inert towards the chemical procedure; depending on the solubility characteristics of the starting substances, this organic liquid may serve either as solvent or as suspending agent. Of these organic liquids e.g. the halogenated hydrocarbons (such as chloroform, carbon tetrachloride, dichloromethane, 1,2-dichloroethane, trichloroethylene, etc.), the aromatic hydrocarbons (such as benzene or toluene), acetone, ether, dioxane, tetrahydrofuran, dimethyl formamide and dimethyl sulfoxide are to be mentioned. The reaction temperature may vary within wide limits, e.g. between 0° C and 180° C, but it is preferred to conduct the reaction at about room temperature. The reaction time varies depending on the starting substances, the solvent and the reaction temperature, and is generally between 1 and 12 hours, preferably between 3 and 6 hours.

According to the preferred process variant a) a solution or a suspension of a tetrahydro-1,4-benzodiazepine-2-one derivative of the formula (II) is treated at room temperature, in the presence of an inorganic acid binding agent (such as magnesium oxide or sodium hydrocarbonate) or a tertiary organic base (such as triethylamine), with a compound of the formula (III), wherein X is preferably chlorine. The progress of the reaction is monitored by thin layer chromatography. When the reaction terminates, the mixture is processed.

The reaction mixture can be processed by various methods epending on the nature of the starting substances, the end-product and the solvent. One may proceed e.g. by removing the optionally separated salts by filtration and evaporating the filtrate to dryness, etc.

When performing process variant a) one may also prepare the starting substance of the formula (III), wherein X is halogen, directly in the reaction mixture e.g. by reacting the appropriate acid with a halogenating agent, such as phosphorous pentachloride, phosphorous trichloride, phosphorous oxychloride, thionyl chloride, etc. The obtained acid halide can be admixed with a solution of a compound of the formula (II), wherein $R_1$, $R_2$ and $R_6$ each have the same meanings as defined above, in an inert organic liquid optionally containing an acid binding agent as well.

If the acid reactant contains an amino substituent, a conventional protecting group is attached to the amino group prior to reacting the acid with the halogenating agent. Of the applicable protecting group e.g. the urethane type protecting groups (such as tert-butoxycarbonyl or an optionally substituted benzyloxycarbonyl group) are to be mentioned. In this event the reaction yields a compound of the formula (I) wherein $R_3$ is an acyl group containing a protected amino substituent. The free amino derivatives can be obtained by removing the protecting groups.

The protecting groups can be split off easily by solvolysis or hydrogenolysis. The solvolytically removable protecting groups (e.g. acyl groups) are split off e.g. with a dilute acid, preferably hydrobromic acid in glacial acetic acid. The hydrogenolytically removable protecting groups are split off preferably by catalytic hydrogenation using a conventional hydrogenating catalyst, preferably a palladium catalyst. This reaction is performed in a solvent or suspending agent, optionally under superatmospheric pressure. As solvent or suspending agent e.g. water, a lower aliphatic alcohol, a cyclic ether such as dioxane or tetrahydrofuran, an aliphatic ether, dimethyl formamide, etc., or the mixtures thereof can be used.

If a compound of the formula (III), wherein X is alkoxy and $R_4$ has the same meanings as defined above, is used as starting substance according to process variant a), it is preferable to conduct the reaction in an inert solvent, such as in an aromatic hydrocarbon (e.g. benzene, toluene, etc.), or in a substituted derivative thereof (e.g. a halogenated aromatic hydrocarbon, such as chlorobenzene). The reaction is performed preferably at elevated temperatures, e.g. between 40° and 200° C. The reaction time varies depending on the nature of the starting substances and the solvent, as well as on the reaction temperature, and may range from about 1 to 10 hours.

According to a preferred method of this latter process variant, a tetrahydro-1,4-benzodiazepine-2-one derivative of the formula (II) is reacted with a compound of the formula (III) wherein X is alkoxy, and the reaction is performed in an organic solvent, such as chlorobenzene, at the boiling point of the solvent.

When a compound of the formula (III), wherein both $R_4$ and X is halogen, preferably chlorine, is used as starting substance, the process yields a compound of the formula (I) wherein $R_3$ is a halocarbonyl, preferably chlorocarbonyl group. If desired, these compounds can be reacted with ammonia or with an amine, such as an aliphatic primary or secondary amine, an araliphatic amine, an aromatic amine or a cyclic amine. Of the aliphatic amines: methylamine, ethylamine, propylamine and butylamine; of the araliphatic amines e.g. benzylamine, α-phenyl-ethylamine and β-phenylethylamine; of the aromatic amines: aniline, α-naphthylamine and β-naphtylamine, and of the cyclic amines pyrrolidine, piperidine, piperazine, 4-methyl-piperazine, morpholine and tetrahydro-1,4-benzodiazepine are to be mentioned.

This reaction is conducted preferably in the presence of an acid binding agent. As acid binding agent e.g. an excess of the amine reactant can be employed, but an inorganic base, such as magnesium oxide, sodium hydrocarbonate, etc. may be used as well.

The reaction is performed preferably in the presence of an inert solvent, such as methanol, ethanol, chloroform, carbon tetrachloride, benzene, aqueous methanol, etc.

If a compound of the formula (IV), wherein $R_5$ is alkali metal and Y stands for a group of the formula NCO- is used as starting substance in process variant b), the compounds of the formula (II) are used preferably in the form of their acid addition salts. The most appropriate acid addition salts are the hydrohalides, such as the hydrochlorides or hydrobromides, but salts formed with other mineral or organic acids, such as phosphoric acid, acetic acid, propionic acid, benzoic acid, etc. may be used as well. According to a preferred method one may proceed by dissolving a compound of the formula (II) in an inert organic solvent, introducing dry gaseous hydrogen chloride into the solution, filtering off the separated hydrochloride, suspending the same without drying in the solvent use for the next reaction step, and then introducing a compound of the formula (IV), wherein $R_5$ stands for alkali metal and Y is a group of the formula NCO-. Any solvent inert towards the reaction, such as the solvents mentioned in connection with process variant a), can be used, but acetic acid has proven to be particularly preferable. The reaction temperature may vary within wide limits and has no decisive significance, but it is preferred to conduct the reaction at about room temperature. Depending on the starting substances, the solvent and the reaction temperature, the reaction time may range from about 20 minutes to about 10 hours.

The above procedure is performed preferably by suspending a mineral acid salt of a compound of the formula (II), preferably a hydrochloride, in an organic liquid, and reacting it at room temperature with potassium cyanate.

If a compound of the formula (IV) wherein $R_5$ stands for an aliphatic, cycloaliphatic or aromatic hydrocarbyl group and Y is a group of the formula —OCN is used as starting substance in process variant b), it is preferable to react this compound with a suspension of a compound of the formula (II), wherein $R_1$, $R_2$ and $R_6$ each have the same meanings as defined above, in an inert organic liquid. As reaction medium e.g. ether, tetrahydrofuran, dioxane or any of the solvents mentioned in connection with process variant a) can be used. It is preferable to use dry (anhydrous) solvents. The reaction temperature may vary within wide limits and has no decisive significance, but it is preferred to conduct the reaction at about room temperature. Depending on the starting substances, the solvent and the reaction temperature, the reaction time may vary within about 1 to 20 hours.

The above procedure is performed preferably by suspending a compound of the formula (II) in an organic solvent, such as in dry ether, and treating this suspension with an alkyl isocyanate at room temperature.

Any of the compounds having the formula (I), wherein $R_2$ is hydrogen, can be alkylated, if desired, to obtain the respective $R_2$ = alkyl derivatives. In this reaction conventional alkylating agents, such as alkyl halides (preferably alkyl iodides) or dialkyl sulfates can be used.

One may proceed by converting first a compound of the formula (I) into its alkali metal derivative, and reacting the thus-obtained alkali metal compound with an appropriate alkylating agent. The alkali metal compound can be prepared e.g. by reacting the appropriate compound of the formula (I) wherein $R_2$ is hydrogen with an alkali metal, alkali hydrode or alkali amide, particularly with sodium or with a sodium compound, at 0° to 150° C in an inert solvent, such as dioxane, dimethyl formamide, benzene or toluene.

When processing the reaction mixture the product is generally obtained in crystalline form. If, however, an oily substance is obtained, this can be crystallized generally very easily using conventional solvents, e.g. aliphatic or cyclic ethers, such as diethyl ether, dioxane, tetrahydrofuran, etc.

If necessary, the compounds of the formula (I) can be subjected to additional purification steps, such as recrystallization. As recrystallization solvent we can use an aliphatic alcohol, such as methanol or ethanol, an aromatic hydrocarbon, such as benzene, a ketone, such as acetone, an aliphatic ester, particularly an alkanecarboxylate such as ethyl acetate, an aliphatic hydrocarbon, particularly a $C_{5-10}$ saturated aliphatic hydrocarbon such as n-hexane, an ether, particularly a dialkyl ether such as diethyl ether, a saturated cyclic ether, such as tetrahydrofuran, acetonitrile, as well as the mixtures thereof (e.g. a mixture of tetrahydrofuran and hexane or a mixture of ethyl acetate and ether).

The process according to the invention provides the compounds of the formula (I) with high yields and in easily identifiable state. The element analysis data of the obtained substances are in good agreement with the calculated values.

Depending on whether a racemic or an optically active starting substance of the formula (II) is used, the end-products of the formula (I) can be obtained in racemic or optically active forms.

The 4-substituted-1,3,4,5-tetrahydro-2H-1,4-benzodiazepine-2-one derivatives according to the invention possess excellent tranquillo-sedative activities. The most valuable representative of these compounds is 1-methyl-4-carbamoyl-5-phenyl-7-chloro-1,3,4,5-tetrahydro-2H-1,4-benzodiazepine-2-one.

The pharmacological tests were carried out according to the following methods:

The tests were performed on CFLP mice of both sexes, weighing 18 to 22 g. In the screen tests the chemicals were administered intraperitoneally, one hour prior to starting the tests. 1-Methyl-4-carbamoyl-5-phenyl-7-chloro-1,3,4,5-tetrahydro-2H-1,4-benzodiazepine-2-one, the most active representative of the compounds according to the invention, as well as the reference substances (Diazepam and Chlorodiazepoxide) were administered orally one hour prior to starting the examinations.

Examination of anit-convulsant activity

1. The first series of examinations was carried out according to the method of Everett and Richards (Everett G. M., Richards R. K.: J. Pharm. Exp. Ther. 81, 402 (1944)). 125 mg./kg. of metrazole were administered subcutaneously to the test animals. 1 hour after the administration the animals protected from tonic extensor spasm and the surviving animals were counted. The $ED_{50}$ values were determined from these data by probit analysis.

2. Maximum electroshock stimulus (100 Hz, 30 V, 0.2 sec.) was applied according to the method of Swinyard et al. (Swinyard E. A., Brown W. C., Goodman, L. S.: J. Pharmacol. 106, 319 (1952)). The animals showing no tonix extension on the hind limb upon stimulus were considered as protected.

Antagonism of strychnine spasm

Tonic extensor spasm was produced by administering an intraperitoneal dosage of 2 mg./kg. of strychnine to the animals (Kerley T. L., Richards A. G., Begley, R. W., Abren, B. E. and Weaver, L. C: J. Pharmacol. Exp. Ther. 132, 360 (1961)). The animals showing no spasm were considered as protected.

Examination of muscle incoordination and ataxia a. Rotarod test: The test was carried out according to the method of Kinnard and Carr (Brit. J. Pharmacol. Exp. Ther. 121, 354 (1957)). The control animals were able to stay for 120 sec. on a rod rotated with a frequency of 12/min. The $ED_{50}$ values were calculated from the percentage of the animals falling down within 120 sec.

b. Traction test: The test was carried out according to the method of Theobald et al. (Arch. int. Pharmacodyn. 148, 560 (1964)). The two anterior limbs of the test animals were placed onto a horizontal rod so as to let the animals clutch the rod. The control animals pulled their hind limbs onto the rod within 5 seconds. The $ED_{50}$ values were calculated from the percentage of the animals showing negative response.

Examination of narcosis potentiating effect

As is known, the liver cannot metabolize sodium barbiturate (Ebert A. G., Yim G. K. W., Miya T. S.: Biochem. Pharmacol. 13, 2161 (1964)). 1 hour after the administration of the compounds to be tested in various dosages, 100 mg./kg. of sodium barbiturate were administered intraperitoneally to the animals, and the $ED_{50}$ values of the compounds under examination were calculated from the percentage of the sleeping animals. (The control animals, receiving only sodium barbiturate in the above dosage, do not fall asleep.)

The hexobarbital narcosis potentiating effect was determined by the method of Rümke et al. (Arch. Int. Pharmacodyn. 146, 10 (1963)) by administering hexobarbital in a dosage of 60 mg./kg. into the tail vein of mice 1 hour after the administration of the compound under examination. The change of sleeping period was expressed in percent related to the controls.

Examination of acute toxicity

The tests were performed at room temperature (24° C), and the death rate of the animals was observed for one week.

The pharmacological data of 1-methyl-4-carbamoyl-5-phenyl-7-chloro-1,3,4,5-tetrahydro-2H-1,4-benzodiazepine-2-one (Compound A) determined in the above tests are listed in Table 1. For comparison, the corresponding data of the reference substances (Diazepam and Chlorodiazepoxide) are also given in the Table.

Table 1

| Method | $ED_{50}$ mg./kg. p.o. (95% confidence limit) | | |
|---|---|---|---|
| | Diazepam | Chlorodiazepoxide | Compound "A" |
| Antimetrazole activity | 0.75 (0.4–1.04) | 2.47 (1.06–6.41) | 0.66 (0.26–0.93) |
| Anti-electroshock activity | 8.29 (5.97–10.98) | 23.5 (15.9–34.3) | 19.3 (13.2–25.5) |
| Antistrychnine activity | 5.71 | 28.4 | 26.0 |
| Rotarod test | 3.1 (1.81–4.2) | 12.2 — | 6.7 (5.5–11.7) |
| Traction test | 4.4 (3.2–5.7) | 31.2 (7.53–52.55) | 26.9 (16.4–41.7) |
| Narcosis potentiating effect | 3.9 (1.7–6.1) | 8.1 (4.41–11.53) | 8.8 (4.0–13.2) |
| Disappearance of righting reflex | 238 (193.9–275.3) | 435.6 (327.2–511.7) | 1400 — |
| Acute toxicity ($LD_{50}$) | 815 — | 850 (691–1040) | 1678 (1516–2564) |

As appears from the data of Table 1, the tetrachor spasm inhibiting effect of 1-methyl-4-carbamoyl-5-phenyl-7-chloro-1,3,4,5-tetrahydro-2H-1,4-benzodiazepine-2-one, a new compound according to the invention, is practically identical to that of Diazepam, whereas the new compound provokes muscle relaxation and sedation only in higher dosages. According to the results, the effects of the new compound are more closely related to those of Chlorodiazepoxide than of Diazepam, but with respect to the dosages provoking muscle incoordination, muscle relaxation, and narcosis potentiation in relation to the dosage provoking anticonvulsive effect, the new compound is clearly more advantageous than the reference substances. The above dosage ratios are listed in Table 2.

Table 2

| Compound | (1) | (2) | (3) |
|---|---|---|---|
| Diazepam | 4.3 | 7.6 | 5.2 |
| Chlorodiazepoxide | 4.9 | 11.5 | 3.3 |
| Compound "A" | 10.2 | 39.4 | 13.3 |

Notes:
(1) Rotarod $ED_{50}$: Antimetrazole $ED_{50}$
(2) Antistrychnine $ED_{50}$ : Antimetrazole $ED_{50}$
(3) Narcosis potentiation $ED_{50}$ : Antimetrazole $ED_{50}$ Summing up, the anticonvulsive effect of 1-methyl-4-carbamoyl-5-phenyl-7-chloro-1,3,4,5-tetrahydro-2H-1,4-benzodiazepine-2-one is identical to that of Diazepam, whereas its sedative and muscle relaxant effects are much lower, and its therapeutic index is more favourable. A single intravenous dosage of 5 mg./kg. of the new compound protects 50% of the animals against metrazole spasm even 7 hours after the administration.

The pharmacological data of some other $N^4$-substituted 1,4-benzodiazepine-2-one derivatives determined according to the above tests are listed in Table 3.

Table 3

| Compound (Ex. No.) | Anti-metrazole ED$_{50}$ | Anti-electroshock ED$_{50}$ i.p. | Rotarod ED$_{50}$ | Hexobarbital potentiation, % | LD$_{50}$ i.p. |
|---|---|---|---|---|---|
| 2  | 12.5 | 14.0 | 20   | 168 | >1600 |
| 13 | 4.9  | 14.0 | 13.5 | 89  | 366.6 |
| 14 | 19.5 | 20   | 20   | 75  | 936   |
| 15 | 20   | 20   | 20   | 93  | >500  |
| 16 | 4.1  | 14.0 | 20   | 104 | 800   |
| 18 | 14.0 | 20   | 20   | 77  | 320   |
| 24 | 13.5 | 20   | 20   | 96  | 271.1 |
| 28 | 7.0  | 20   | 20   | 125 | 312.4 |
| 31 | 14.0 | 20   | 20   | 85  | >1600 |
| 33 | 3.4  | 14.0 | 23   | 110 | 687.6 |
| 55 | 1.65 | 10.0 | 7.0  | 368 | 611.2 |
| 56 | 2.2  | 8.4  | 13.0 | 112 | 661.2 |

Note: all dosages are expressed as mg./kg.

Some of the compounds according to the invention passes slightly lower antimetrazole activities than Chlorodiazepoxide, it should be noted, however, that unlike Diazepam, these compounds show no or only minor sedative or muscle relaxing effects.

The effective dosage of the compounds according to the invention is generally about 2 to 20 mg., preferably 2.5 to 15 mg. per day. This amount of active agent can be added either in a single dosage or in subdivided form in equal dosages. The actual dosages should always be determined on the basis of the needs of the patient and the experiences of the physician, in accordance with the type and severity of the disorders. The invention is by no means restricted to the dosage limits mentioned above.

The compounds of the general formula (I), wherein $R_1$, $R_2$, $R_3$ and $R_6$ each have the same meanings as defined above, can be converted into orally, parenterally or enterally administerable pharmaceutical compositions using conventional non-toxic, inert solid or liquid carriers and/or auxiliary substances. The pharmaceutical compositions may contain one or more compound(s) of the formula (I), or they may contain the compounds of the general (I) in combination with other pharmaceutically active substances. As carrier, e.g. water, gelatine, lactose, starch, pectine, magnesium stearate, stearic acid, talc, vegetable oils (such as peanut oil, olive oil, etc.), gum arabic, polyalkylene glycols, vazeline, etc. can be applied. The active agents can be formulated to obtain solid compositions (e.g. tablets, lozenges, dragees, capsules, pills, etc.) or liquid preparations (e.g. oily or aqueous solutions, suspensions, emulsions, syrups, soft gelatine capsules, injectable aqueous or oily solutions or suspensions, etc.) The amount of the solid carrier substance may vary over wide limits; a single dosage unit contains preferably about 0.025 to 1 g. of solid carrier. The compositions may contain optionally usual pharmaceutical auxiliary agents, such as preservatives, stabilizing agents, wetting agents, emulsifying agents, salts for adjusting the osmotic pressure, buffers, flavouring agents, aroma substances, etc.

The pharmaceutical compositions can be prepared by the usual pharmaceutical procedures, including e.g. screening, mixing, granulation, pressing and/or dissolution. If necesssary, the compositions can be subjected to further pharmaceutical processing steps (e.g. sterilization).

The invention is elucidated in detail by the aid of the following non-limiting Examples.

The purity grades of the produced substances were determined by thin layer chromatography. The $R_f$ values were determined on a Stahl "C" silica gel plate (Merck), using as eluent one of the following systems: (1) 1:4:8 mixture of n-hexane, ethyl acetate and chloroform; (2) 1:1:8 mixture of n-hexane, acetic acid and chloroform; (3) 9:1 mixture of chloroform and methanol. The spots were developed by the chlorine-tolidine technique. The melting points were determined in a dr.Tottoli-type apparatus (the melting points given in the Examples are non-corrected values). In some instances the structures of the product were identified by IR or NMR spectroscopy or by mass spectrometry.

EXAMPLE 1

1-Methyl-4-ethoxycarbonyl-5-phenyl-7-chloro-1,3,4,5-tetrahydro-2H-1,4-benzodiazepine-2-one 2.8 ml. (0.02 moles) of triethylamine are added to a solution of 5.73 g. (0.02 moles) of 1-methyl-5-phenyl-7-chloro-1,3,4,5-tetrahydro-2H-1,4-benzodiazepine-2-one in 30 ml. of chloroform, and a solution of 2 ml. of ethyl chloroformate in 10 ml. of chloroform is added to the stirred mixture at room temperature. After 3 hours of stirring 1.4 ml. (0.01 moles) of triethylamine and a solution of 1 ml. of ethyl chloroformate in 5 ml. of chloroform are added to the reaction mixture. The reaction mixture is stirred for an additional 2 hours and then evaporated to dryness under reduced pressure. The residue is crystallized from ethanol. 6.7 g. (92.5%) of crystalline 1-methyl-4-ethoxycarbonyl-5-phenyl-7-chloro-1,3,4,5-tetrahydro-2H-1,4-benzodiazepine-2-one are obtained; m.p.: 173°–174° C, $R_f^1 = 0.5$.

Analysis:

Calculated for $C_{19}H_{19}O_3N_2Cl$ (M = 358.84): C: 63.6% H: 5.3% N: 7.8% Found: C: 63.5% H: 5.5% N: 7.9%

Similarly the following compounds were prepared from the appropriate starting substances:

Example 2

4-Ethoxycarbonyl-5-phenyl-7-nitro-1,3,4,5-tetrahydro-2H-1,4-benzodiazepine-2-one Yield: 75%. Melting point: 130°–132° C (after recrystallization from ethanol). $R_f^1 = 0.3$. Analysis: Calculated for $C_{18}H_{17}O_5N_3$ (M = 355.36): C: 60.8% H: 4.8% N: 11.8% Found: C: 60.9% H: 5.3% N: 11.7%.

EXAMPLE 3

1-Methyl-4-t-butyoxycarbonyl-5-phenyl-7-chloro-1,3,4,5-tetrahydro-2H-1,4-benzodiazepine-2-one Yield: 90%. Melting point: 177-178° C (after recrystallization from ethanol). $R_f^1 = 0.55$. Analysis: Calculated for $C_{21}H_{23}O_3N_2Cl$ (M = 386.89): C: 65.2% H: 6.0% N: 7.2% Found: C: 65.2% H: 6.2% N: 6.9%

Example 4

4-t-Butoxycarbonyl-5-phenyl-7-nitro-1,3,4,5-tetrahydro-2H-1,4-benzodiazepine-2-one Yield: 65.2%. Melting point: 138-139° C (after recrystallization from ethanol.) $R_f^1 = 0.5$. Analysis: Calculated for $C_{20}H_{21}O_5N_3$ (M = 383.41): C: 62.7% H: 5.5% N: 11.0% Found: C: 63.2% H: 5.8% N: 10.7%

EXAMPLE 5

1-Methyl-4-p-chlorobenzyloxycarbonyl-5-phenyl-7-chloro-1,3,4,5-tetrahydro-2H-1,4-benzodiazepine-2-one Yield: 82.3%. Melting point: 153-154° C (after recrystallization from ethanol). $R_f^1 = 0.6$. Analysis: Calculated for $C_{24}H_{20}O_3N_2Cl_2$ (M = 455.36): C: 63.3% H: 4.4% N: 6.1% Found: C: 63.3% H: 5.0% N: 6.4%

EXAMPLE 6

4-p-Chlorobenzyloxycarbonyl-5-phenyl-7-nitro-1,3,4,5-tetrahydro-2H-1,4-benzodiazepine-2-one Yield: 67.8%. Melting point: 203-205° C (after recrystallization from ethanol). $R_f^1 = 0.5$. Analysis: Calculated for $C_{23}H_{18}O_5N_3Cl$ (M = 451.88): C: 61.2% H: 4.0% N: 9.1% Found: C: 61.5% H: 4.1% N: 9.1%

EXAMPLE 7

1-Methyl-4-menthyloxycarbonyl-5-phenyl-7-chloro-1,3,4,5-tetrahydro-2H-1,4-benzodiazepine-2-one 0.2 g. of magnesium oxide and 1.21 g. (0.0055 moles) of menthyloxycarbonyl chloride are added to a solution of 1.34 g. (0.005 moles) of 1-methyl-5-phenyl-7-chloro-1,3,4,5-tetrahydro-2H-1,4-benzodiazepine-2-one in 20 ml. of acetone, and the mixture is stirred overnight. Next day carbon is added to the mixture, the suspension is filtered, and the filtrate is evaporated to dryness. The oily residue is dissolved in 20 ml. of ethyl acetate, the solution is shaken with 3×5 ml. of 0.1 N hydrochloric acid, the organic phase is washed with water until neutral, then dried over sodium sulfate. The drying agent is filtered off, and the filtrate is evaporated. The residue is admixed with hexane, and the solids are filtered off. 0.82 g. of 1m-methyl-4-methyloxycarbonyl-5-phenyl-7-chloro-1,3,4,5-tetrahydro-2H-1,4-benzodiazepine-2-one, melting at 144-144.5° C, are obtained. The obtained substance is recrystallized from a mixture of ethanol and water. $R_f^1 = 0.8$.

Similarly are prepared the following compounds from the appropriate starting substances:

EXAMPLE 8

1-Methyl-4-menthyloxycarbonyl-5-phenyl-7-nitro-1,3,4,5-tetrahydro-2H-1,4-benzodiazepine-2-one The reaction is conducted in absolute tetrahydrofuran. Yield: 39%. Melting point: 206-207° C (after recrystallization from ethanol). $R_f^1 = 0.75$.

EXAMPLE 9

4-Menthyloxycarbonyl-5-phenyl-7-chloro-1,3,4,5-tetrahydro-2H-1,4-benzodiazepine-2-one The reaction is conducted in acetone. Yield: 57%. Melting point: 220-220° C. $R_f^1 = 0.8$.

EXAMPLE 10

1-Methyl-4-carbamoyl-5-phenyl-7-chloro-1,3,4,5-tetrahydro-2H-1,4-benzodiazepine-2-one Dry gaseous hydrochloric acid is led for some minutes into a solution of 5.72 g. (0.02 moles) of 1-methyl-5-phenyl-7-chloro-1,3,4,5-tetrahydro-2H-1,4-benzodiazepine-2-one in 20 ml. of chloroform, then the separate hydrochloride is filtered off and suspended in 200 ml. of acetic acid. 4.5 g. of solid potassium cyanate are added to the suspension, and the mixture is stirred, for 2 hours at room temperature. During this time a clear solution is formed. The solution is cooled, neutralized with concentrated ammonia, the separated product is filtered off, and washed with water. 6.0 g. (94.9%) of 1-methyl-4-carbamoyl-5-phenyl-7-chloro-1,3,4,5-tetrahydro-2H-1,4-benzodiazepine-2-one are obtained. The product melts at 217°-219° C after recrystallization from ethanol. $R_f^1 = 0.28$.

Analysis: Calculated for $C_{17}H_{16}O_2N_3Cl$ (M = 329.76): C: 61.95% H: 4.9% N: 12.7% Found: C: 61.90% H: 4.9% N: 13.0%

Similarly are prepared the following compounds from the appropriate starting substances:

EXAMPLE 11

4-Carbamoyl-5-phenyl-7-nitro-1,3,4,5-tetrahydro-2H-1,4-benzodiazepine-2-one

Yield: 73.5%. Melting point: 239-241° C (after recrystallization from ethanol). $R_f^1 = 0.22$. Analysis: Calculated for $C_{16}H_{14}N_4O_4$ (M = 326.32): C: 58.85% H: 4.3% N: 17.2% Found: C: 59.1% H: 4.5% N: 16.8%

EXAMPLE 12

4-Carbamoyl-5-phenyl-1,3,4,5-tetrahydro-2H-1,4--benzodiazepine-2-one

Yield: 74.2%. Melting point: 227°-228° C (after recrystallization from ethanol). $R_f^1 = 0.45$. Analysis: Calculated for $C_{16}H_{15}O_2N_3$ (M = 281.30): C: 68.3% H: 5.4% N: 15.0% Found: C: 68.0% H: 5.2% N: 15.0%

EXAMPLE 13

4-Carbamoyl-5-phenyl-7-chloro-1,3,4,5-tetrahydro-2H-1,4-benzodiazepine-2-one Yield: 98.5%. Melting point: 242°-245° C (after recrystallization from ethanol). $R_f^1 = 0.35$. Analysis: Calculated for $C_{16}H_{14}O_2N_3Cl$ (M = 315.75): C: 60.75% H: 4.5% N: 15.3% Found: C: 60.4% H: 4.2% N: 15.0%

EXAMPLE 14

4-Methylcarbamoyl-5-phenyl-7-nitro-1,3,4,5-tetrahydro-2H-1,4-benzodiazepine-2-one 5.6 g. (0.02 moles) of 7-nitro-5-phenyl-1,3,4,5-tetrahydro-2H-1,4-benzodiazepine-2-one are suspended in 25 ml. of dry ether, and 4.8 ml. (0.08 moles) of methyl isocyanate are added to the suspension. The reaction mixture is stirred at room temperature for 16 hours, thereafter the solid crystalline substance is filtered off and washed with ether. 6.03 g. (97.6%) of 4-methylcarbamoyl-5-phenyl-7-nitro-1,3,4,5-tetrahydro-2H-1,4-benzodiazepine-2-one are obtained, m.p.: 176°-180° C. After recrystallization from ethanol, the product melts at 179°-180° C. $R_f^1 = 0.4$.

Analysis: Calculated for $C_{17}H_{16}O_4N_4$ (M = 312.31): C: 60.0% H: 4.7% N: 16.45% Found: C: 60.3% H: 4.6% N: 16.2%.

Similarly are prepared the following compounds from the appropriate starting substances:

EXAMPLE 15

4-Methylcarbamoyl-5-phenyl-1,3,4,5-tetrahydro-2H-1,4-benzodiazepine-2-one

Yield: 96.4%. Melting point: 140°-144° C (after recrystallization from acetonitrile). $R_f^1 = 0.4$. Analysis: Calculated for $C_{17}H_{17}O_2N_3$ (M = 295.33): C: 69.15% H: 5.8% N: 14.3% Found: C: 68.97% H: 5.7% N: 14.5%

EXAMPLE 16

4-Methylcarbamoyl-5-phenyl-7-chloro-1,3,4,5-tetrahydro-2H-1,4-benzodiazepine-2-one Yield: 88.6% Melting point: 235°-238° C (after recrystallization from ethanol). $R_f^1 = 0.35$. Analysis: Calculated for $C_{17}H_{16}O_2N_3Cl$ (M = 329.78): C: 61.85% H: 4.9% N: 12.7% Found: C: 61.58% H: 4.5% N: 12.7%

EXAMPLE 17

4-Ethylcarbamoyl-5-phenyl-7-nitro-1,3,4,5-tetrahydro-2H-1,4-benzodiazepine-2-one Yield: 72.5%. Melting Point: 185°–189° C (after recrystallization from ethanol). $R_f = 0.2$. Analysis: Calculated for $C_{18}H_{18}O_4N_4$ (M = 354.36): C: 61.0% H: 5.1% N: 15.8% Found: C: 61.3% H: 4.3% N: 16.0%

EXAMPLE 18

4-n-Butylcarbamoyl-5-phenyl-7-nitro-1,3,4,5-tetrahydro-2H-1,4-benzodiazepine-2-one Yield: 82.3 %. Melting point: 204°–208° C (after recrystallization from acetonitrile). $R_f = 0.3$. Analysis: Calculated for $C_{20}H_{22}O_4N_4$ (M = 382.4): C: 62.75% H: 5.8% N: 14.7% Found: C: 62.95% H: 6.2% N: 14.8%

EXAMPLE 19

4-n-Butylcarbamoyl-5-phenyl-1,3,4,5-tetrahydro-2H-1,4-benzodiazepine-2-one

Yield: 87.9%. Melting point: 202°–204° C (after recrystallization from acetonitrile). $R_f = 0.65$. Analysis: Calculated for $C_{20}H_{23}O_2N_3$ (M = 337.41): C: 71.3% H: 6.9% N: 12.5% Found: C: 71.1% H: 6.3% N: 12.5%

EXAMPLE 20

4-n-Butylcarbamoyl-5-phenyl-7-chloro-1,3,4,5-tetrahydro-2H-1,4-benzodiazepine-2-one Yield: 91.5%. Melting point: 226°–229° C (after recrystallization from ethanol). $R_f = 0.75$. Analysis: Calculated for $C_{20}H_{22}O_2N_3Cl$ (M = 371.86): C: 64.6% H: 6.0% N: 11.3% Found: C: 64.8% H: 6.1% N: 11.4%

EXAMPLE 21

4-Phenylcarbamoyl-5-phenyl-7-nitro-1,3,4,5-tetrahydro-2H-1,4-benzodiazepine-2-one Yield: 63.3%. Melting point: 222°–224° C (after recrystallization from a mixture of tetrahydrofuran and hexane). $R_f = 0.6$. Analysis: Calculated for $C_{22}H_{18}O_4N_4$ (M: 402.41): C: 65.8% H: 4.5% N: 14.0% Found: C: 65.8% H: 4.7% N: 13.7%

EXAMPLE 22

4-Phenylcarbamoyl-5-phenyl-1,3,4,5-tetrahydro-2H-1,4-benzodiazepine-2-one

Yield: 84.8%. Melting point: 227°–228° C (after recrystallization from acetonitrile). $R_f = 0.72$. Analysis: Calculated for $C_{22}H_{19}O_2N_3$ (M = 357.39): C: 74.0% H: 5.4% N: 11.8% Found: C: 73.6% H: 6.4% N: 11.6%

EXAMPLE 23

4-Phenylcarbamoyl-5-phenyl-7-chloro-1,3,4,5-tetrahydro-2H1,4-benzodiazepine-2-one Yield: 82.2%. Melting point: 232°–237° C (after recrystallization from acetonitrile.) $R_f = 0.7$. Analysis: Calculated for $C_{22}H_{18}O_2N_3Cl$ (M = 391.83): C: 67.45% H: 4.6% N: 10.7% Found: C 67.8% H: 5.3% N: 11.05%

EXAMPLE 24

1-Methyl-4-(1-methyl-benzylcarbamoyl)-5-phenyl-7-chloro-1,3,4,5-tetrahydro-2H-1,4-benzodiazepine-2-one Yield: 75.7%. Melting point: 163°–165° C (after recrystallization from ethyl acetate). $R_f = 0.6$. Analysis: Calculated for $C_{25}H_{24}O_2N_3Cl$ (M = 433.92): C: 69.15% H: 5.6% N: 9.7% Found: C: 68.9% H: 5.6% N: 9.7%

EXAMPLE 25

4-(1-Methyl-benzylcarbamoyl)-5-phenyl-7-chloro-1,3,4,5-tetrahydro-1,4-benzodiazepine-2-one Yield: 78%. Melting point: 170°–172° C (after recrystallization from a mixture of ethyl acetate and ether) $R_f = 0.55$. Analysis. Calculated for $C_{24}H_{22}O_2N_3Cl$ (M = 419.90): C: 68.6% H: 5.25% N: 10.0% Found: C: 68.2% H: 4.9% N: 10.4%

EXAMPLE 26

1-Methyl-4-aminoacetyl-5-phenyl-7-chloro-1,3,4,5-tetrahydro-2H-1,4-benzodiazepine-2-one 2.8 g. (13.4 mmoles) of benzyloxycarbonyl-glycine are suspended in 27 ml. of dry ether, and 3 g. (15 mmoles) of phosphorous pentachloride are added in portions to the suspension at 0° C. The mixture is stirred for 20 minutes, and thereafter a solution of 2.86 g. (10 mmoles) of 1-methyl-5-phenyl-7-chloro-1,3,4,5-tetrahydro-2H-1,4-benzodiazepine-2-one in 15 ml. of dry tetrahydrofuran containing 9 ml. of triethylamine is added dropwise to the obtained solution. The reaction mixture is stirred in an ice bath for 6 hours, and evaporated to dryness under reduced pressure. The oily residue is dissolved in 100 ml. of chloroform, the chloroform solution is washed with 3 × 50 ml. of water, 1 × 50 ml. of sodium bicarbonate solution and with water again, dried, and evaporated to dryness under reduced pressure. The oily residue is covered with ether, upon which is solidifies. 4.28 g. (90%) of 1-methyl-4-(N-benzyloxycarbonyl-aminoacetyl)-5-phenyl-7-chloro-1,3,4,5-tetrahydro-2H-1,4-benzodiazepine-2-one are obtained; m.p.: 58°–160° C (after recrystallization from ethanol), $R_f = 0.60$. Analysis: Calculated for $C_{26}H_{24}O_4N_3Cl$ (M = 477.93): C: 65.2% H: 5.1% N: 8.8% Found: C: 65.5% H: 4.9% N: 8.9%

21 ml. of a 5N hydrobromic acid solution in glacial acetic acid are poured onto 4.24 g. (8.9 mmoles) of the above substance, and the mixture is stirred at room temperature for 0.5 hours. Thereafter 60 ml. of dry ether are added to the solution, upon which the hydrobromide of the product separates. The separated substance is dissolved in 10 ml. of water, and the solution is rendered alkaline (pH = 8) with concentrated ammonia. The separated crystals are filtered off, washed with cold water, dried, and crystallized from 6 ml. of benzene. 2.44 g. (79.6%) of 1-methyl-4-aminoacetyl-5-phenyl-7-chloro-1,3,4,5-tetrahydro-2H1,4-benzodiazepine-2-one are obtained; m.p: 158°–160° C, $R_f = 0.3$.

Analysis: Calculated for $C_{18}H_{18}O_2N_3Cl$ (M = 343.81): C: 62.8% H-5.3% N: 12.25% Found: C: 62.8% H: 5.3% N: 12.3%

EXAMPLE 27

1-Methyl-4-chloroacetyl-5-phenyl-7-chloro-1,3,4,5-tetrahydro-2H-1,4-benzodiazepine-2-one 3 g. of magnesium oxide are added to a solution of 2.87 g. (0.01 mmoles) of 1-methyl-5-phenyl-7-chloro-1,3,4,5-tetrahydro-2H-1,4-benzodiazepine-2-one in 30 ml. of chloroform, and a solution of 1.2 ml. (0.018 moles) of chloroacetyl chloride in 4 ml. of chloroform is added to the vigorously stirred mixture. After 3 hours of stirring at room temperature the magnesium salt is filtered off, washed with 20 ml. of chloroform, and the filtrate is evaporated to dryness under reduced pressure. The residue is crystallized from acetone. 2.68 g. (8.14%)

of 1-methyl-4-chloroacetyl-5-phenyl-7-chloro-1,3,4,5-tetrahydro-2H-1,4-benzodiazepine-2-one are obtained; m.p.: 197°-200° C; $R_f^2 = 0.5$.

Analysis: Calculated for $C_{18}H_{16}O_2N_2Cl_2$ (M = 365.24): C: 59.75% H: 4.4% N: 7.65% Found: C: 59.7% H: 3.9% N: 7.7%

Similarly are prepared the following compounds from the appropriate starting substances:

EXAMPLE 28

1-Methyl-4-acetyl-5-phenyl-7-chloro-1,3,4,5-tetrahydro-2H-1,4-benzodiazepine-2-one Yield: 74.5%. Melting point: 201°-203° C (after recrystallization from ethanol). $R_f^2 = 0.45$.

Analysis: Calculated for $C_{18}H_{17}O_2N_2Cl$ (M = 328.79): C: 65.7% H: 5.2% N: 8.5% Found: C: 65.4% H: 5.2% N: 8.5%

EXAMPLE 29

4-Acetyl-5-phenyl-7-nitro-1,3,4,5-tetrahydro-2H-1,4-benzodiazepine-2-one

Yield: 98%. Melting point: 258°-260° C (after recrystallization from acetonitrile). $R_f^2 = 0.45$. Analysis: Calculated for $C_{17}H_{15}O_4N_3$ (M = 325.31): C: 62.7% H: 4.6% N: 12.95% Found: C: 62.6% H: 4.7N: 12.75%

EXAMPLE 30

1-Methyl-4-phenylacetyl-5-phenyl-7-chloro-1,3,4,5-tetrahydro-2H-1,4-benzodiazepine-2-one Yield: 94.7%. Melting point: 228°-231° C (after recrystallization from ethanol). $R_f^2 = 0.8$. Analysis: Calculated for $C_{24}H_{21}O_2N_2Cl$ (M = 404.88): C: 71.25% H: 5.2% N: 6.9% Found: C: 71.25% H: 5.4% N: 6.9%

EXAMPLE 31

1-Methyl-4-(o-chlorobenzoyl)-5-phenyl-7-chloro-1,3,4,5-tetrahydro-2H-1,4-benzodiazepine-2-one Yield: 88%. Melting point: 250°-253° C (after recrystallization from acetonitrile). $R_f^2 = 0.8$. Analysis: Calculated for $C_{23}H_{18}O_2N_2Cl_2$ (M = 425.30): C: 64.95% H: 4.3% N- 6.6% Found: C: 64.95% H: 3.7% N: 6.5%

EXAMPLE 32

1-Methyl-4-(p-chlorobenzoyl)-5-phenyl-7-chloro-1,3,4,5-tetrahydro-2H-1,4-benzodiazepine-2-one Yield: 96.5%. Melting point: 238°-240° C (after recrystallization from acetonitrile). $R_f^2 = 0.8$. Analysis: Calculated for $C_{28}H_{18}O_2N_2Cl_2$(M = 425.30): C: 64.95% H: 4.3% N: 6.6% Found: C: 64.74% H: 4.3% N: 6.7%

EXAMPLE 33

1-Methyl-4-formyl-5-phenyl-7-chloro-1,3,4,5-tetrahydro-2H-1,4-benzodiazepine-2-one 6 ml. of ethyl formate are added to a solution of 1.4 g. (5 mmoles) of 1-methyl-5-phenyl-7-chloro-1,3,4,5-tetrahydro-2H-1,4-benzodiazepine-2-one in 5 ml. of chlorobenzene, and the reaction mixture is maintained at the boiling point of the solvent for 3 hours. Thereafter the solvent is evaporated under reduced pressure, and the oily residue is solidified by treating it with 20 ml. of dry ether. 108 g. (68.6%) of 1-methyl-4-formyl-5-phenyl-7-chloro-1,3,4,5-tetrahydro-2H-1,4-benzodiazepine-2-one are obtained; m.p.: 167°-169° C. The melting point does not change after recrystallization from ethanol. $R_f^2 = 0.5$.

Analysis: Calculated for $C_{17}H_{15}O_2N_2Cl$ (M = 314.76): C: 64.8% H: 4.8% N: 8.9% Found: C: 63.0% H: 5.9% N: 8.9%

Similarly are prepared the following compounds from the appropriate starting substances:

EXAMPLE 34

4-Formyl-5-phenyl-7-nitro-1,3,4,5-tetrahydro-2H-1,4-benzodiazepine-2-one

Yield: 90.7%. Melting point: 258°-261° C (after recrystallization from acetone). $R_f^2 = 0.4$. Analysis: Calculated for $C_{16}H_{13}O_4N_3$ (M = 311.29): C: 61.7% H: 4.2% N: 13.5% Found: C: 62.0% H: 4.2% N: 13.3%

EXAMPLE 35

4-Formyl-5-phenyl-7-amino-1,3,4,5-tetrahydro-2H-1,4-benzodiazepine-2-one

Yield: 67.5%. Melting point: 239°-241° C (after recrystallization from 95% ethanol). $R_f^2 = 0.5$. Analysis: Calculated for $C_{16}H_{15}O_2N_3$ (M = 281.32): C: 68.3168.00% H: 5.37% N: 14.94% Found: C: 68,00% H: 4.95% N: 14.65%

The following compounds are prepared from the appropriate starting substances as described in Example 27:

EXAMPLE 36

1-Methyl-4-acryloyl-5-phenyl-7-chloro-1,3,4,5-tetrahydro-2H-1,4-benzodiazepine-2-one Yield: 85.2%. Melting point: 169°-171° C (after recrystallization from ethanol). $R_f^2 = 0.75$. Analysis: Calculated for $C_{19}H_{17}O_2N_2Cl$ (M = 340.81): C: 66.96% H: 5.03% N: 8.22%

Found: C: 67.26 % H: 5.09 % N: 8.49 %

EXAMPLE 37

4-Acryloyl-5-phenyl-7-nitro-1,3,4,5-tetrahydro-2H-1,4-benzodiazepine-2-one

Yield: 72.6%. Melting point: 225°-227° C (after recrystallization from ethanol). $R_f^2 = 0.70$. Analysis: Calculated for $C_{18}H_{15}O_4N_3$ (M = 337.34): C: 64.09% H: 4.48% N: 12.46% Found: C: 64.25% H: 4.65% N: 12.32%

EXAMPLE 38

4-Cyclopentylcarbonyl-5-phenyl-7-nitro-1,3,4,5-tetrahydro-2H-1,4-benzodiazepine-2-one Yield: 80.0%. Melting point: 248°-251° C with decomposition (after recrystallization from ethanol). $R_f^2 = 0.66$. Analysis: Calculated for $C_{21}H_{21}N_3O_4$ (M = 379.42): C: 66.48% H: 5.58% N: 11.08% Found: C: 66.50% H: 5.22% N: 10.84%

EXAMPLE 39

1-Methyl-4-cyclopentylcarbonyl-5-phenyl-7-chloro-1,3,4,5-tetrahydro-2H-1,4-benzodiazepine-2-one Yield: 80.0%. Melting point: 229°-232° C with decomposition (after recrystallization from ethanol). $R_f^2 = 0.78$. Analysis: Calculated for $C_{22}H_{23}O_2N_2N_2Cl$ (M = 282.89): C: 69.01% H: 6.06% N: 7.32% Found: C: 68.68% H: 5.75% N: 7.30%

EXAMPLE 40

1-Methyl-4-cyclohexylcarbonyl-5-phenyl-7-chloro-1,3,4,5-tetrahydro-2H-1,4-benzodiazepine-2-one Yield: 74.67 %. Melting point: 189°–191° C (after recrystallisation from ethanol). $R_f^2 = 0.75$. Analysis: Calculated for $C_{23}H_{25}O_2N_2Cl$ (M = 396.92): C: 69.60% H: 6.25% N: 7.06% Found: C: 70.00% H: 6.20% N: 7.18%

EXAMPLE 41

4-Cyclohexylcarbonyl-5-phenyl-7-chloro-1,3,4,5-tetrahydro-2H-1,4-benzodiazepine-2-one Yield: 70.0%. Melting point: 181°–183° C (after recrystallization from ethanol). $R_f^2 = 0.80$. Analysis: Calculated for $C_{22}H_{23}O_2N_2Cl$ (M = 382.88): C: 69.01% H: 6.06% N: 7.32% Found: C: 69.35% H: 5.85% N: 7.04%

The following compounds are prepared from the appropriate starting substances as described in Example 14:

EXAMPLE 42

1-Methyl-4-(1-naphthylcarbamoyl)-5-phenyl-7-chloro-1,3,4,5-tetrahydro-2H-1,4-benzodiazepine-2-one Yield: 72%. Melting point: 271°–273° C (after recrystallization from dimethyl formamide). $R_f^2 = 0.80$. Analysis: Calculated for $C_{27}H_{22}O_2N_3$ (M = 455.95): C: 71.13% H: 4.96% N: 9.22% Found: C: 71.52% H: 4.52% N: 9.18%

EXAMPLE 43

4-(1-Naphthylcarbamoyl)-5-phenyl-7-nitro-1,3,4,5-tetrahydro-2H-1,4-benzodiazepine-2-one Yield: 95%. Melting point: 194°–196° C (after recrystallization from ethyl acetate). $R_f^2 = 0.70$. Analysis: Calculated for $C_{26}H_{20}O_4N_4$ (M = 452.47): C: 69.02% H: 4.56% Ni: 12.38% Found: C: 69.36% H: 4.38% N: 12.22%

EXAMPLE 44

1-Methyl-4-carbamoyl-5-phenyl-7-chloro-1,3,4,5-tetrahydro-2H-1,4-benzodiazepine 2-one 0.16 g. (6.85 mmoles) of metallic sodium are dissolved in 2 ml. of absolute methanol, and a suspension of 0.9 g. (2.86 mmoles) of 4-carbamoyl-5-phenyl-7-chloro-1,3,4,5-tetrahydro-2H-1,4-benzodiazepine-2-one in 50 ml. of absolute methanol is added to the solution at room temperature, with stirring. The suspension is stirred at room temperature for 30 minutes, and then evaporated under reduced pressure. The oily residue is dissolved in 9 ml. of dimethyl formamide, and 0.48 ml. of methyl iodide are added to the stirred solution at room temperature. The mixture is stirred for additional 2 hours, then diluted with 50 ml. of water and extracted with 3 × 10 ml. of chloroform. The chloroform extracts are combined, dried over sodium sulfate, filtered, and the filtrate is evaporated under reduced pressure, to obtain 0.85 g. of a residue, which is recrystallized from ethanol. 0.75 g. (79.5%) of 1-methyl-4-carbamoyl-5-phenyl-7-chloro-1,2,4,5-tetrahydro-2H-1,4-benzodiazepine-2-one are obtained; m.p.: 217°–220° C.

EXAMPLE 45

1-Methyl-4-(1-morpholinocarbonyl)-5-phenyl-7-chloro-1,3,4,5-tetrahydro-2H-1,4-benzodiazepine-2-one 1 ml. of morpholine is added to a suspension of 1.7 g (4.8 mmoles) of 1-methyl-4-chlorocarbonyl-5-phenyl-7-chloro-1,3,4,5-tetrahydro-2H-1,4-benzodiazepine-2-one in 5 ml. of methanol, and the mixture is stirred at room temperature for one hour. During this time a clear solution is formed. 25 ml. of water are added slowly to the cooled solution. The separated substance is filtered off, washed with water, dried, and recrystallized from ethanol. 1.78 g. (89%) of 1-methyl-4-(1-morpholinocarbonyl)-5-phenyl-7-chloro-1,3,4,5-tetrahydro-2H-1,4-benzodiazepine-2-one are obtained; m.p.: 184°–185° C, $R_f^2 = 0.45$.

Similarly are prepared the following compounds from the appropriate starting substances:

EXAMPLE 46

1-Methyl-4-(1-piperidinocarbonyl)-5-phenyl-7-chloro-1,3,4,5-tetrahydro-2H-1,4-benzodiazepine-2-one Yield: 87.5%. Melting point: 136.5°–137° C (after recrystallization from 95% ethanol). $R_f^2 = 0.68$.

EXAMPLE 47

1-Methyl-4-(4-methyl-1-piperidinocarbonyl)-5-phenyl-7-chloro-1,3,4,5-tetrahydro-2H-1,4-benzodiazepine-2-one Yield: 95.7%. Melting point: 240.5°–242° C (after recrystallization from acetonitrile). $R_f^2 = 0.53$.

EXAMPLE 48

1-Methyl-4-hydrazinocarbonyl-5-phenyl-7-chloro-1,3,4,5-tetrahydro-2H-1,4-benzodiazepine-2-one Yield: 87%. Melting point: 187°–189° C (after recrystallization from a mixture of benzene and chloroform). $R_f^2 = 0.19$.

EXAMPLE 49

Di-(1-methyl-2-oxo-5-phenyl-7-chloro-1,3,4,5-tetrahydro-2H-1,4-benzodiazepin-4-yl)-ketone 1 g. of 1-methyl-5-phenyl-7-chloro-1,3,4,5-tetrahydro-2H-1,4-benzodiazepine-2-one and 1 g. of magnesium oxide are added to a solution of 0.8 g. (2.29 mmoles) of 1-methyl-4-chlorocarbonyl-5-phenyl-7-chloro-1,3,4,5-tetrahydro-2H-1,4-benzodiazepine-2-one in 10 ml. of chloroform, and the mixture is stirred at 40° C overnight. Thereafter the inorganic salts are filtered off, washed with 10 ml. of chloroform, and the chloroform solution is stirred with 10 ml. of 2n hydrochloric acid. The hydrochloride of the non-reacted base separates. The salt is filtered off, and the filtrate is washed with 5 ml. of 2.5% aqueous sodium hydrocarbonate solution and with water. The chloroform solution is dried and evaporated. The obtained dry residue is recrystallized from ethanol. 0.91 g. (66.2%) of di-(1-methyl-2-oxo-5-phenyl-7-chloro-1,3,4,5-tetrahydro-2H-1,4-benzodiazepine-4-yl)-ketone are obtained; m.p.: 263°–266° C, $R_f^2 = 0.71$.

EXAMPLE 50

4-Chlorocarbonyl-5-phenyl-7-chloro-1,3,4,5-tetrahydro-2H-1,4-benzodiazepine-2-one 0.84 g. of dry, solid sodium hydrocarbonate are added to a suspension of 1.36 g. (5 mmoles) of 5-phenyl-7-chloro-1,3,4,5-tetrahydro-2H-1,4-benzodiazepine-2-one in 60 ml. of absolute benzene, and 15 ml. of a 10% phosgene solution in benzene are added dropwise to the mixture at 10°–15° C. The mixture is stirred at 10°–15° C for one hour and then at room temperature overnight. The inorganic salts are filtered off and washed with 50 ml. of acetone. The organic phase is evaporated, and the dry residue is recrystallized from benzene. 1.08 g. (64.5%) of 4-chlorocarbonyl-5-phenyl-7-chloro-1,3,4,5-tetrahydro-2H-1,4-benzodiazepine-2-one are obtained; m.p.: 181°–184° C, $R_f^2 = 0.82$.

Similarly are prepared the following compounds from the appropriate starting substances:

EXAMPLE 51

1-Methyl-4-chlorocarbonyl-5-phenyl-7-chloro-1,3,4,5-tetrahydro-2H-1,4-benzodiazepine-2-one Yield: 91%. Melting point: 186°–187° C (after recrystallization from benzene). $R_f^2 = 0.8$.

EXAMPLE 52

(−)-1-Methyl-4-chlorocarbonyl-5-phenyl-7-chloro-1,3,4,5-tetrahydro-2H-1,4-benzodiazepine-2-one Starting substance: (+)-1-methyl-5-phenyl-7-chloro-1,3,4,5-tetrahydro-2H-1,4-benzodiazepine-2-one. Yield: 67.5%. Melting point: 201°–203.5° C (after recrystallization from acetone). $(\alpha)_D^{25} = -646.5°$ (c = 1, chloroform).

EXAMPLE 53

(−)-1-Methyl-4-carbamoyl-5-phenyl-7-chloro-1,3,4,5-tetrahydro-2H-1,4-benzodiazepine-2-one 2.1 g. (7.32 mmoles) of (+)-1-methyl-5-phenyl-7-chloro-1,3,4,5-tetrahydro-2H-1,4-benzodiazepine-2one are dissolved in 20 ml. of benzene. 1.26 g. of solid sodium bicarbonate are added to the solution, and then 22 ml. of a 10% solution of phosgene in benzene are added dropwise at 10 to 15° C. The mixture is stirred for 2 hours, then 10 ml. of a 10% solution of ammonia in methanol are added, and the mixture is stirred at room temperature overnight. The separated inorganic salts are filtered off, and the filter cake is washed with benzene. The filtrate is evaporated to dryness under reduced pressure, and the residue is recrystallized from ethanol. 2.12 g. (87.5%) of (−)-1-methyl-4-carbamoyl-5-phenyl-7-chloro-1,3,4,5-tetrahydro-2H-1,4-benzodiazepine-2-one are obtained; m.p.: 214°–217° C, $[\alpha]_D^{25} = -616.5°$ (c = 1, chloroform).

EXAMPLE 54

1-Methyl-4-carbamoyl-5-phenyl-7-chloro-1,3,4,5-tetrahydro-2H-1,4-benzodiazepine-2-one A suspension of 1.7 g. (4.87 mmoles) of 1-methyl-4-chlorocarbonyl-5-phenyl-7-chloro-1,3,4,5-tetrahydro-2H-1,4-benzodiazepine-2-one in 3.5 ml. of concentrated ammonia and 7 ml. of methanol is stirred at room temperature overnight. The mixture is diluted with 30 ml. of water, the separated crude product is filtered off, and recrystallized from ethanol without drying. 1.16 g. (72%) of 1-methyl-4-carbamoyl-5-phenyl-7-chloro-1,3,4,5-tetrahydro-2H-1,4-benzodiazepine-2-one are obtained; m.p.: 212°–215° C.

The following compounds are prepared from the appropriate starting substances as described in Example 14:

EXAMPLE 55

(+)-1-Methyl-4-carbamoyl-5-phenyl-7-chloro-1,3,4,5-tetrahydro-2H-1,4-benzodiazepine-2-one Starting substance: (−)-1-methyl-5-phenyl-7-chloro-1,3,4,5-tetrahydro-2H-1,4-benzodiazepine-2-one (prepared as described in Hungarian Patent No. 160,769). Yield: 77.4%. Melting point: 215°–217° C (after recrystallization from ethanol). $[\alpha]_D^{25} = +613.9° \pm 2°$ (c = 1, in chloroform).

EXAMPLE 56

(−)-1-Methyl-4-carbamoyl-5-phenyl-7-chloro-1,3,4,5-tetrahydro-2H-1,4-benzodiazepine-2-one Starting substance: (+)-1-methyl-5-phenyl-7-chloro-1,3,4,5-tetrahydro-2H-1,4-benzodiazepine-2-one (prepared as described in Hungarian Patent No. 160,769). Yield: 89.2%. Melting point: 215°–217° C. $[\alpha]_D^{25} = -612.8° \pm 2°$ (c = 1, chloroform).

The compounds prepared according to the invention can be converted into orally administerable pharmaceutical compositions as follows:

EXAMPLE 57

Preparation of tablets

Tablets of the following composition are prepared according to the usual tabletting procedure:

| | |
|---|---|
| 1-Methyl-4-carbamoyl-5-phenyl-7-chloro-1,3,4,5-tetrahydro-2H-1,4-benzodiazepine-2-one | 0.010 g. |
| Lactose | 0.226 g. |
| Starch | 0.125 g. |
| Gelatine | 0.004 g. |
| Talc | 0.012 g. |
| Stearine | 0.004 g. |
| Ultraamylopectine | 0.012 g. |
| Colloidal silicic acid | 0.002 g. |

What we claim is:

1. 4-Ethoxycarbonyl-5-phenyl-7-nitro-1,3,4,5-tetrahydro-2H-1,4-benzodiazepine-2-one.
2. 1-Methyl-4-formyl-5-phenyl-7-chloro-1,3,4,5-tetrahydro-2H-1,4-benzodiazepine-2-one.

* * * * *